(12) United States Patent
Hirota et al.

(10) Patent No.: US 6,360,606 B2
(45) Date of Patent: *Mar. 26, 2002

(54) PIEZOELECTRIC SENSOR DEVICE AND A METHOD FOR DETECTING CHANGE IN ELECTRIC CONSTANTS USING THE DEVICE

(75) Inventors: Toshikazu Hirota, Kuwana; Takao Ohnishi, Nishikasugai-gun; Keizo Miyata, Ichinomiya; Kazuyoshi Shibata, Mizunami, all of (JP)

(73) Assignee: NGK Insulators, Ltd., Nagoya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/267,562

(22) Filed: Mar. 12, 1999

(30) Foreign Application Priority Data

Mar. 27, 1998 (JP) ............................................. 10-081500

(51) Int. Cl.[7] .............................................. G01N 11/16
(52) U.S. Cl. ......................... 73/579; 73/54.24; 73/32 A; 310/324
(58) Field of Search ............... 73/54.24, 54.25, 73/54.26, 54.27, 579, 61.49, 61.75, 61.79, 64.53, 32 A; 310/324

(56) References Cited

U.S. PATENT DOCUMENTS 5,889,351 A    3/1999    Ikumura et al. ............ 310/321

FOREIGN PATENT DOCUMENTS

| EP | 0 714 022 A2 | 5/1996 |
| EP | 0 809 105 A1 | 11/1997 |
| JP | 8-201265 | 8/1996 |

OTHER PUBLICATIONS

Patent Abstracts of Japan, vol. 97, No. 11, Nov. 28, 1997 & JP 09178642 A (NGK Insulators, Ltd.), Jul. 11, 1997, abstract.

*Primary Examiner*—John E. Chapman
(74) *Attorney, Agent, or Firm*—Burr & Brown

(57) ABSTRACT

A piezoelectric sensor device has a piezoelectric body vibrator consisting of the piezoelectric body which is sandwiched by a pair of electrodes, a power source which applies a voltage to the piezoelectric body vibrator so as to get excited for vibration, means for monitoring electric constants to detect changes in electric constants accompanied by vibration of the piezoelectric body. The change in electric constants in the piezoelectric body is detected as a change in frequency for vibration of the piezoelectric body corresponding to an electric constant under the determined conditions. The piezoelectric sensor device has a means to obtain the frequency value from frequencies at not less than two points giving a determined electric constant. According to the piezoelectric sensor device the dispersion in measured values due to change in vibration aptness of vibration system and the polarization state of piezoelectric body vibrator can be made smaller.

14 Claims, 6 Drawing Sheets

… …

PIEZOELECTRIC SENSOR DEVICE AND A METHOD FOR DETECTING CHANGE IN ELECTRIC CONSTANTS USING THE DEVICE

BACKGROUND OF THE INVENTION AND RELATED ART STATEMENT

This invention relates to a sensor device which uses a piezoelectric body vibrator to measure features of fluid in terms of coefficient of viscosity, specific gravity, density, etc.

The quality of fluid products, such as chemicals, foods, lubricating oil, car wax, etc., is controlled by their manufacturing process, and is guaranteed in terms of performance. It is important, therefore, to measure the features of such fluids in terms of the coefficient of viscosity, specific gravity, density, etc. In recent years, in order to measure the features of such fluids, it is proposed to make use of a piezoelectric body vibrator, as disclosed in U.S. Pat. No. 5,889,351. The disclosed device measures coefficient of viscosity of fluids and includes a piezoelectric body vibrator consisting of a piezoelectric body sandwiched by electrodes, a power source for applying a voltage for exciting vibration of the piezoelectric body vibrator, and an electric constant monitoring means for detecting changes in electric constants accompanied by vibration of the piezoelectric body.

In such a device, the piezoelectric body vibrator is made to vibrate in a fluid, which vibration is inhibited by mechanical resistance applied to the vibrator based on the viscosity of the fluid. Changes in electric constants of the piezoelectric body structuring the vibrator are detected, and the coefficient of viscosity of the fluid can be detected. Incidentally, the change in electric constants in the piezoelectric body is normally detected as a change in frequency of vibration in the piezoelectric body corresponding to a certain electric constant (e.g., phase) under predetermined conditions. Conventionally, for example, as shown in FIG. 6, a predetermined phase (θ) value (e.g., 70°) neighboring the resonance frequency ($f_{max}$) is adopted since it is difficult to detect the exact resonance frequency. The frequency $f_a$ where the phase value becomes "a" (e.g., 70°) is obtained at one point at either side (left in the present example) of $f_{max}$. By precalibration, a vibrator vibrating in a fluid at frequency "fa" and phase "a" can be said to have a corresponding viscosity.

Incidentally, even though fluids to be measured may be the same in terms of coefficient of viscosity and specific gravity, when the vibration characteristics of the piezoelectric vibrator change due to changes in the polarization state, additives to restrain vibration, changes in temperature, and the like, a change occurs in the shape of the frequency vs. phase curve. When the vibration characteristics change, in most cases, as shown in FIG. 7, the value of $f_{max}$ remains unchanged, but the corresponding phase values change. For example, when θ is "a", the frequency will dramatically change from $f_a$ to $f_a'$, resulting in erroneous measured values in the above-described technique.

In addition, since the piezoelectric body is initially polarized, that is, maintained at room temperature or higher temperatures under the Curie point for several hours to several days to stabilize the polarization state after an electric field with a level higher than a coercive field has been applied for a comparatively long period at a temperature close to the Curie point, the piezoelectric body to be used for a sensor device is extraordinarily highly sensitive. On the other hand, however the piezoelectric body maintains poor stability in many cases, and therefore, even if the polarization process described above is provided, a change in polarization state (deterioration in polarization state, depolarization) is apt to occur due to application of stress, passage of time, and the like. And, when such a change in polarization state occurs, as shown in FIG. 8, not only does the frequency vs. phase curve become flatter, as in FIG. 7, but it also shifts to higher frequencies. Accordingly, $f_{max}$ shifts to $f'_{max}$, thus resulting in greater error in measured values.

SUMMARY OF THE INVENTION

The purpose of the present invention, which has been made taking such conventional problems into consideration, is to provide a piezoelectric sensor device in which dispersion in measured values due to changes in vibration characteristics of the vibration system and the polarization state of the piezoelectric body can be reduced, as well as a method for detecting changes in electric constants of the sensor device.

According to the present invention, there is provided a piezoelectric sensor device comprising a piezoelectric body vibrator consisting of a piezoelectric body which is sandwiched by a pair of electrodes, a power source which applies a voltage to the piezoelectric body vibrator so as to vibrate the vibrator, means for monitoring electric constants to detect changes in electric constants accompanied by vibration of the piezoelectric body, the change in electric constants in the piezoelectric body being detected as a change in frequency for vibration of the piezoelectric body corresponding to an electric constant under predetermined conditions, and means for obtaining the resonant frequency, $f_{max}$, of the vibrator from frequencies at not less than two points at a predetermined electric-constant value.

Also according to the present invention, there is provided a method for detecting change in electric constants comprising: using the above-described piezoelectric sensor device, and obtaining $f_{max}$ as an average value of two points, which give the same electric constant value.

DETAILED DESCRIPTION OF PREFERRED EMBODIMENTS

The piezoelectric sensor device according to the present invention includes means for obtaining the value of the resonant frequency $f_{max}$ of vibration of a piezoelectric body vibrator from frequencies at not less than two points at a predetermined electric constant. And by comprising such means, in the detecting method using a device of the present invention, for example as shown in FIG. 1, it becomes possible to obtain $f_{max}$ as an average value $(f_{aL}$ and $f_{aR})/2$ from $f_{aL}$ and $f_{aR}$ at the same predetermined phase "a".

Figure 1:
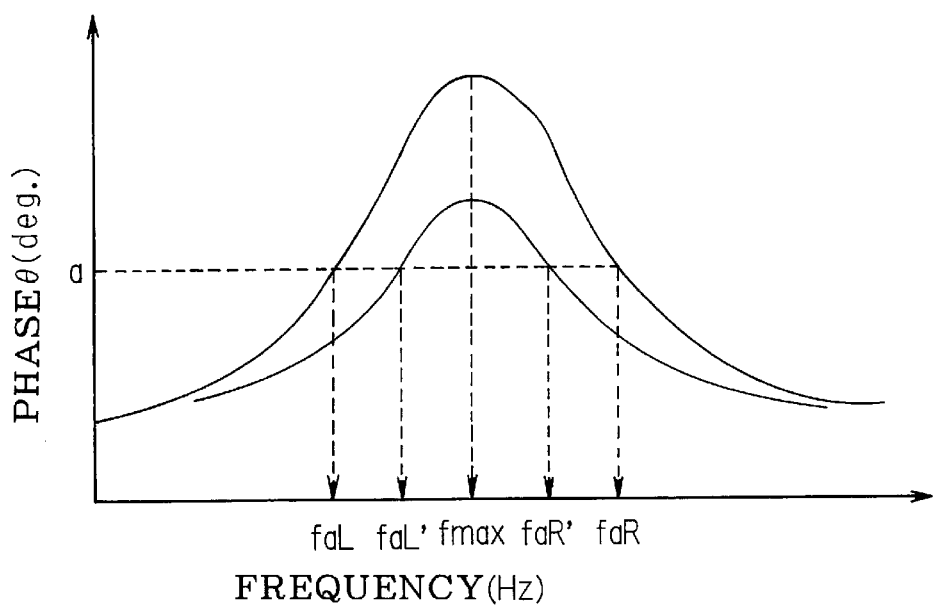
FIG. 1 is an explanatory view explaining the detecting method using the device of the present invention based on a graph plotting change in phase corresponding to frequency.
Figure 2:
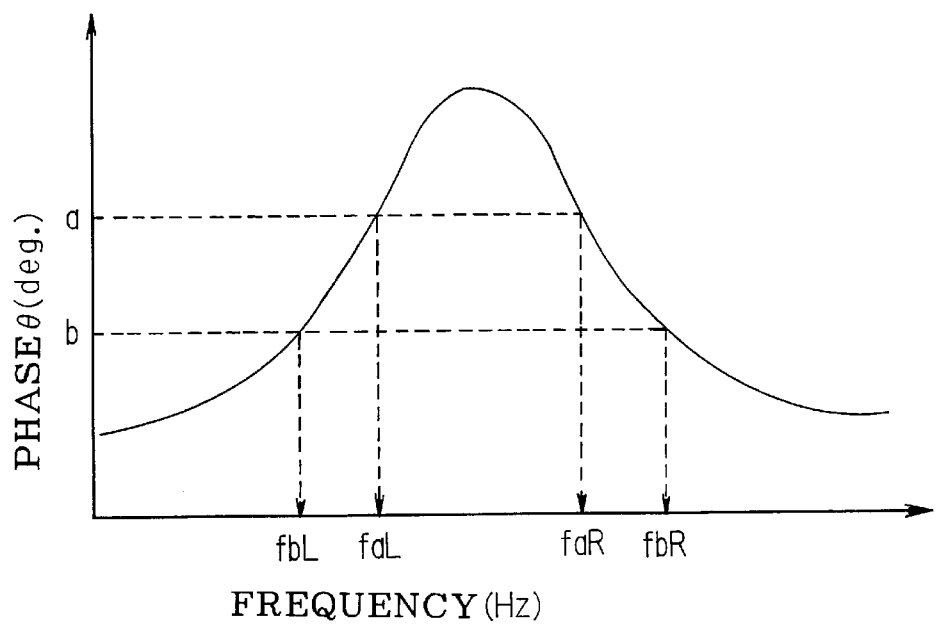
FIG. 2 is an explanatory view explaining the detecting method using the device of the present invention based on the graph plotting change in phase corresponding to frequency.

Obtaining a frequency value like this, even if the frequencies at two points which result in the same electric constant phase "a" may change from $f_{aL}$ and $f_{aR}$ to $f_{aL}'$ and $f_{aR}'$ when the shape of the plot changes as shown in FIG. 1, without any change in the frequency $f_{max}$ giving the maximum value, $(f_{aL}+f_{aR})/2$ and $(f_{aL}'+f_{aR}')/2$ will yield the same value. Therefore, compared with the conventional measurement obtaining the frequency at one point, it is influenced little due to changes in vibration characteristics of the vibration system. Also, FIG. 2 is an example using two predetermined phases wherein by the device of the present invention, frequencies $f_{aL}$ and $f_{aR}$ at two points giving the same phase "a", as well as frequencies $f_{bL}$ and $f_{bR}$ at two points giving the same phase "b" were obtained, and their average value $(f_{aL}+f_{aR}+f_{bL}+f_{bR})/4$ was obtained as the resonance frequency value.

Figure 8:
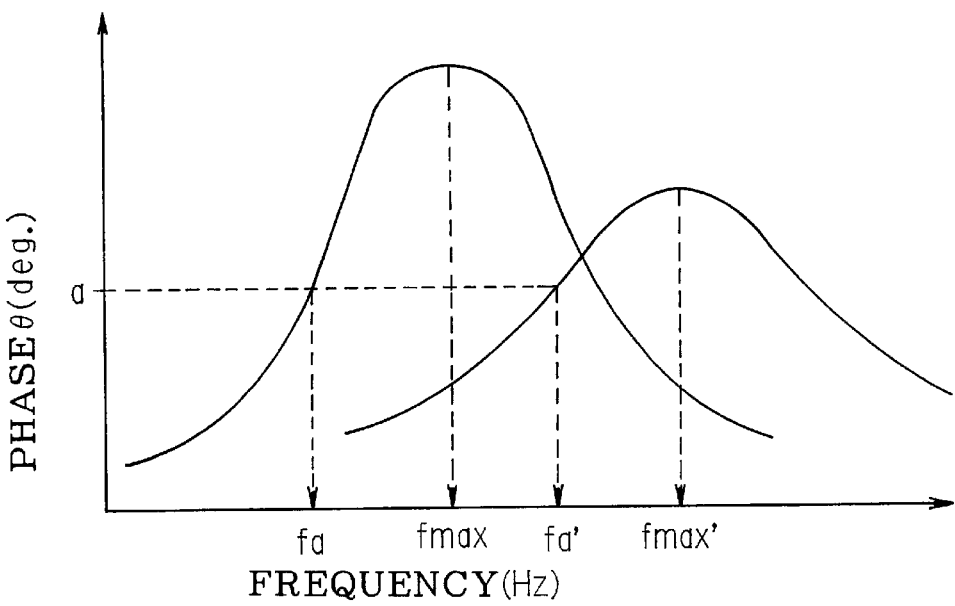
FIG. 8 is a graph plotting the change in phase corresponding to frequency showing the state when the polarization sate changes largely.

Incidentally, the above-described device as well as the detecting method using it is effective where the value of frequency $f_{max}$ giving the maximum value of phase (θ) scarcely changes as a result of changes in only the vibration characteristics of the vibration system, while in the cases where the polarization state of a piezoelectric body vibrator changes largely, as shown in FIG. 8, and the frequency under which θ takes the largest value changes from $f_{max}$ to $f_{max}'$, dispersion will arise in the detected frequency as a result of its influence. Therefore, in order to control such influence, the sensor device of the present invention preferably comprises polarization processing means to hold the polarization state of a piezoelectric body vibrator stable.

Thus, as mentioned above, the piezoelectric body vibrator to be used for a sensor device such as in the present invention has a quality that its polarization state is apt to change easily, and this quality was a cause of leading to dispersion in measured values. It is possible, however, to take advantage of this quality and thus easily subject the piezoelectric body to polarization before proceeding with measurement. By arranging for polarization of the piezoelectric body vibrator to take place before each measurement, it becomes possible to hold constant the polarization state of the piezoelectric body vibrator during measurement. Incidentally, the fact that the piezoelectric body is easily polarized extends its utility especially with combinations of materials and structures for the sensor element to be described later.

As a polarization processing means as described above, a power source making polarization processing take place in the piezoelectric body vibrator can be presented as an example, and by conducting frequency measurements while the power source applies an electric field surpassing the coercive field of the piezoelectric body (i.e., the electric field strength at which polarization occurs), the polarization state of the piezoelectric body vibrator can be held constant and the change in $f_{max}$ as shown in FIG. 8 can be controlled. Although it is preferred to conduct measurements while always polarizing in this way, there are problems such as degradation in resolution capability with respect to controlling vibration, and durability of the piezoelectric body vibrator is adversely influenced since a voltage is always applied to the piezoelectric body vibrator.

In order to avoid such problems, it may be possible to avoid continuous application of an electric field to the piezoelectric body during measurement, but to proceed with polarization processing for only a predetermined time period whenever frequency is being measured. As for the polarization processing in this case, it is preferable to apply an electric field surpassing the coercive field of the piezoelectric body at room temperature for not more than three seconds, more preferably not more than one second. In addition, it is also preferable to apply an electric field surpassing the coercive field of the piezoelectric body similarly at room temperature for not more than three seconds, more preferably not more than one second in the negative polarity, and thereafter further apply an electric field for not more than three seconds, more preferably not more than one second in the positive polarity. In this way, when an electric field is applied in the opposite polarity in advance, stability of polarization is improved. Incidentally, the reason why the respective application time periods of electric fields are set preferably for not more than three seconds is that an instant application of electric field is sufficient and longer application leads to lengthening measurement time as well as increasing the power to be consumed.

In addition, when such polarization processing takes place, it is preferable to proceed with measurement after a certain time period has lapsed after the polarization process. This means that the timing for measurement to be proceeded with after polarization processing should be kept constant. Therefore, the above-described certain time period, which is not limited in particular, and with the time period from the time of conclusion of the polarization processing to the time for measurement being kept constant, the measurement may take place just after the polarization processing, or measurement may take place some predetermined time after the polarization processing. However, measurement should take place preferably during the period between immediately after polarization processing and 60 seconds thereafter, and further preferably during the period between 0.1 second to three seconds after polarization processing since it will be practically inconvenient if too much time is required from completion of polarization processing until when measurement takes place, which could lead to lengthening the measurement time period.

Incidentally, when such polarization processing has been conducted, electric charge is stored in a piezoelectric body after polarization processing, and such electric charge becomes a primary factor causing dispersion in measured values. Therefore, in addition to the above-described polarization processing means, the device of the present invention should preferably comprise means for discharging the electric charge stored in the piezoelectric body after the polarization processing (discharging processing means). Such discharging processing means may be means for simply making a short circuit take place between both terminals of the piezoelectric body vibrator, or may be means for making discharge take place gradually with a resistance inserted between both terminals.

By conducting measurement after proceeding with discharging processing on a piezoelectric body after polarization processing by such a discharging processing means, it becomes possible to further decrease dispersion in measured values. Incidentally, when such discharging processing is conducted, it is preferable that measurement is conducted after a certain time period has lapsed after discharging processing similarly as in the case where the above described polarization processing is conducted. This means that the timing for measurement to be conducted after discharging processing is kept constant.

In detecting frequency of vibration of the piezoelectric body corresponding to electric constants under predetermined conditions, in the mechanism to detect change in either one of the electric constants and the frequency against the remaining other one, means to substitute the other value corresponding to one value with a value to be calculated from the other some values corresponding to some values within a range having that one value as a center are also preferably comprised in the sensor device of the present invention.

Figure 9:
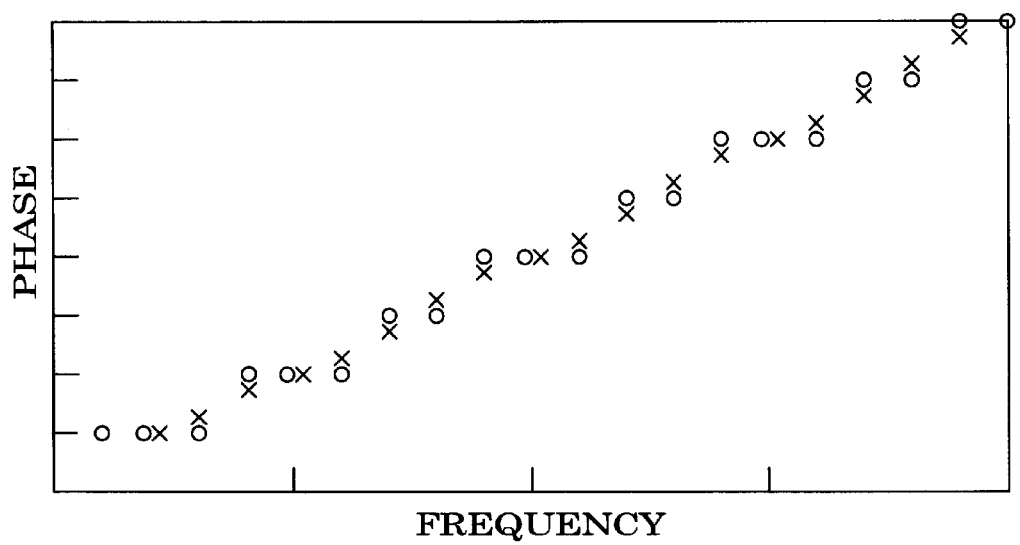
FIG. 9 is a graph plotting the change in phase corresponding to frequency showing the state when measurement resolution capability for electric constants remains low.

For example, in the case where the measurement resolution capability of phase is lower and a plurality of frequencies giving the same phase exist as shown in the graph in FIG. 9 plotting changes in phase vs. frequency, the accuracy for measurement of frequency is deteriorated and dispersion grows larger. In such cases, by the above-described means, as shown with X symbols in the drawing, the value of phase corresponding to a frequency is substituted with a value to be calculated from the phase corresponding to frequencies within a certain range around it, thereby the measurement resolution capability for the apparent phase is improved, and as a result, the accuracy on measurement of frequency is improved and dispersion is decreased. Incidentally, in the X symbols in FIG. 9, the value of phase is substituted by the running average consisting of three points with two points sandwiching the remaining point, however, the above-described calculation method is not limited thereto.

As aforementioned, the present invention has been explained based on phase as an example of an electric constant, however, the electric constant is not limited to phase, but any of loss factor, phase, resistance, reactance, conductance, susceptance, inductance, and capacitance is applicable. Any means for monitoring an electric constant which is to be comprised in the device of the present invention will do if it detects any of those electric constants.

Figure 10:
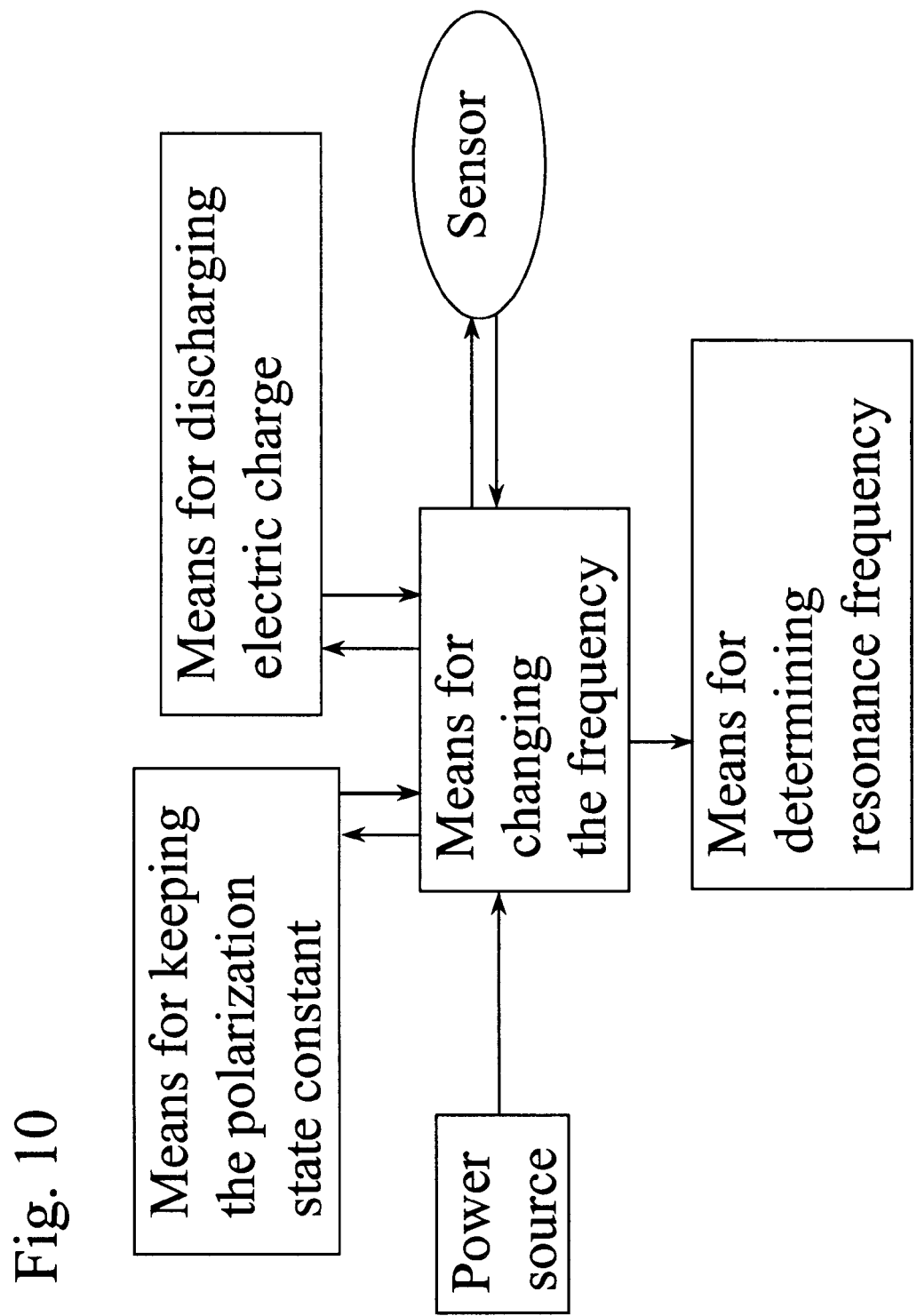
FIG. 10 is a block diagram showing a preferred system according to the present invention.

FIG. 10 shows a block diagram of a system in accordance with a preferred embodiment of the present invention, which employs all of the features discussed earlier herein.

Figure 3:
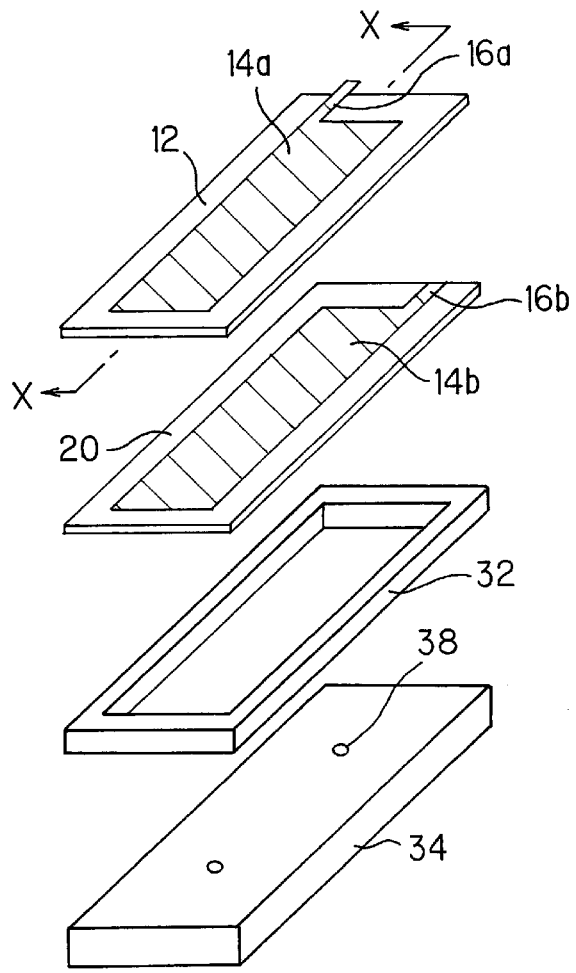
FIG. 3 is an exploded perspective view showing one example of the sensor element equipped in the device of the present invention.

In the sensor device of the present invention, the piezoelectric body vibrator preferably constructs a sensor element integrated with a base body having the following structure. The base body has thin-plate-shaped vibration part on one surface of which the piezoelectric body vibrator is fixed and a cavity which can lead a fluid to the other surface of the vibration part. FIG. 3 is an exploded perspective view showing one example of the sensor element which has been constructed by making such a base body and piezoelectric body vibrator together into one body, and FIG. 4 a cross-section view along the XX line therein.

A base body 30 is structured by laminating a thin-plate-shaped vibration plate 20, a frame 32 and a base plate 34 having a through hole 38. The base body 30 structured in this way has a vibration part 22 in the shape of thin walled portion, and a piezoelectric body vibrator 10 is fixed on one surface of this vibration part 22. The shape of the vibration part 22 is not limited in particular, but various shapes can be adopted with their thickness being preferably between 1 and 100 $\mu$m and further preferably between 3 and 50 $\mu$m and further preferably between 5 and 20 $\mu$m.

In addition, the base body 30 has a cavity 36, and this cavity 36 is formed so as to be capable of leading the fluid to be measured, the features of which are to be measured, to the other surface of the vibration part 22 (the surface located in the opposite side of the surface where the piezoelectric body vibrator has been fixed) via a through hole 38. The shape of the cavity 36 is not limited in particular. Moreover, the through hole 38 may be one or may be plural in terms of its number as long as a fluid to be measured can be introduced into the cavity 36.

The piezoelectric body vibrator 10 has been formed where a pair of electrodes 14a and 14b are joined onto both the surfaces of a piezoelectric body 12. Lead parts 16a, 16b of electrodes 14a, 14b are connected to a power source to excite the piezoelectric body vibrator 10 for vibration, and to a means for monitoring electric constants to detect changes in electric constants accompanied by vibration of the piezoelectric body 12. When a voltage is applied to the piezoelectric body 12 via electrodes 14a, 14b, the polarization takes place, and the piezoelectric body vibrator 10 together with the vibration part 22 is bent and vibrated in the direction of thickness of the piezoelectric body vibrator 10 as well as of the vibration part 22. The thickness of the piezoelectric body 12 is preferably between 1 and 100 $\mu$m and further preferably between 5 and 50 $\mu$m and furthermore preferably between 5 and 30 $\mu$m.

The piezoelectric body 12 may be dense or porous, and in the case of being porous, the porosity rate is preferably not more than 40 percent. In addition, the piezoelectric body 12 may consist of one layer or may have a lamination structure with two or more layers. When the lamination structure with two or more layers is adopted, each layer may be established in a lying position or may be established in a standing position. The electrodes 14a, 14b are supposed to have an appropriate thickness, however, the thickness is preferably between 0.1 and 50 $\mu$m.

In the sensor element having such a structure, when the fluid to be measured is made to flow into the cavity 36 from the through hole 38 to contact the vibration part 22, and a voltage is applied to the piezoelectric body 12 so that vibration takes place in the piezoelectric body 12 and the vibration part 22, the vibration form of the piezoelectric body 12 changes, in accordance with changes in the coefficient of viscosity, further the electric constants of the piezoelectric body change in accordance with changes in the vibration form of the piezoelectric body 12. The present invention provides measurement of features of a fluid to be measured, by thus relating the features of the fluid to be measured to the vibration form of a piezoelectric body, and detecting changes in electric constants accompanied by changes in that vibration form with a means to monitor the electric constants.

Next, the material of each component of the sensor element will be explained. The base body 30 is preferably made of ceramics. For example, stabilized zirconium oxide, aluminum oxide, magnesium oxide, mullite, aluminum nitride, silicon nitride, and glass, may be used. The stabilized zirconium oxide is preferable since it has higher mechanical strength, higher toughness, and lower chemical reactivity with the piezoelectric body and electrodes in spite of the small thickness of the vibration part.

For a piezoelectric body 12, piezoelectric ceramics can be preferably used, however, electrostrictive ceramics or ferroelectric ceramics may also be used. As ceramics to be used as a piezoelectric body, choices to be adopted are, for example, ceramics containing lead zirconate, lead magnesium niobate, lead nickel niobate, lead zinc niobate, lead manganese niobate, lead antimony stannate, lead titanate, lead manganese tungstate, lead cobalt niobate, barium titanate, or ingredients with any of these in combination.

Those ceramics which are oxides of lanthanum, calcium, strontium, molybdenum, tungsten, barium, niobium, zinc, nickel, and manganese, or any combination of these, or other chemical compounds may be further added to the aforementioned ceramics as appropriate. For example, it is preferred to use ceramics consisting of lead magnesium niobate, lead zirconate, and lead titanate as the principal ingredient and further including lanthanum and strontium, and the like.

The electrode 14a is preferably a solid at room temperature and formed of a conductive metal. Choices to be adopted are, for example, a single metal or an alloy containing aluminum, titanium, chromium, ferrum, cobalt, nickel, copper, zinc, niobium, molybdenum, ruthenium, rhodium, silver, tin, tantalum, tungsten, iridium, platinum, gold, lead, and the like.

The electrode 14b to be made contact-connected with diaphragm 20 is preferably joined together without using adhesive, and therefore, is a metal having a high melting point, and may be exemplified with a single metal or alloy containing platinum, ruthenium, rhodium, palladium, iridium, titanium, chromium, molybdenum, tantalum, tungsten, nickel, cobalt, and the like in optional combination. Among them, platinum metal such as platinum, rhodium, and palladium, or those with silver-platinum, platinum-palladium, and the like alloy as principal ingredients containing them can be especially preferably used since the resulting substance has a higher melting point and higher chemical stability. Moreover, cermets containing these metals with higher melting points and ceramics such as alumina, zirconium oxide, silicon oxide, glass, may be used.

Next, a method for forming a sensor element will be explained. The base body can be made as one body by laminating a shaped layer being a green sheet or a green tape with thermal pressure attachment, and subsequent sintering. For example, in the base body 10 shown in FIG. 3 and FIG. 4, three green sheets or green tapes processed in the respective shapes of diaphragm 20, frame 32 and base plate 34 are laminated.

The layers may also be formed by compression molding, casting, or injection molding, and the space may be provided by cutting, machining, laser processing, or pressing. The shaped layers do not need to have the same thickness, however, their respective shrinkages due to sintering are preferably set to the same level.

As a method for forming a piezoelectric body vibrator 10 on one surface of the vibration part 22, there is a method in which a piezoelectric body is molded by a compression molding method using metal molds or a tape molding method using slurry materials, and the piezoelectric body is laminated to the vibration part of the base body with thermal compression attachment, and then the parts are simultaneously sintered, thereby the base body and the piezoelectric body are formed. In this case, the electrode needs to be formed in advance in the base body or a piezoelectric body by the film forming method which is described later.

Sintering temperature of the piezoelectric body is appropriately set according to material, and in general 800 to 1400° C., or preferably 1000 to 1400° C. In this case, in order to control the composition of a piezoelectric body, it is preferred to conduct sintering under the presence of an evaporation source of the components of the piezoelectric body material.

On the other hand, in the film forming method, electrode 14b, piezoelectric body 12, and electrode 14a are laminated in this order at the vibration part 22 to form the piezoelectric body vibrator 10. The publicly known film forming methods, for example, a thick film method such as screen printing, a brushing method such as dipping, a thin film method such as ion beam, sputtering, vacuum deposition, ion plating, chemical vapor deposition (CVD), and plating, and so forth are appropriately used, however they are not intended to limit the scope of the invention in any way. Among them, the screen printing method is preferable since it provides stable manufacturing.

Forming a piezoelectric body like this by way of a film forming method is particularly preferable since the piezoelectric body is superior in reliability and reproducibility and moreover easily integrated because it allows the piezoelectric body vibrator and the vibration part to be connected as an integral unit without using adhesive. The shape of such film may also form an appropriate pattern. Pattern forming may be employed, using screen printing method, photolithography method, and pattern forming may also be employed removing the unnecessary portions by way of laser machining, slicing, and mechanical process such as ultrasonic machining.

Respective films (12, 14a, 14b) may be made to form a one-body structure with the base body subject to thermal processing each time the respective film is formed, or after these films are formed, these films may be formed as one body with the base body subject to simultaneous thermal processing.

EXAMPLES

Further details of the invention will be explained according to examples as follows, to which, however, the invention should not be deemed to be limited.

Example 1

Figure 4:
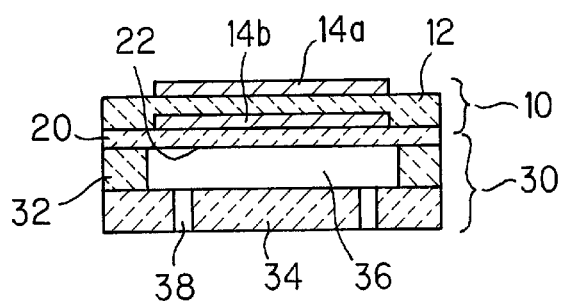
FIG. 4 is a cross-section view along the XX line in FIG. 3.
Figure 5:
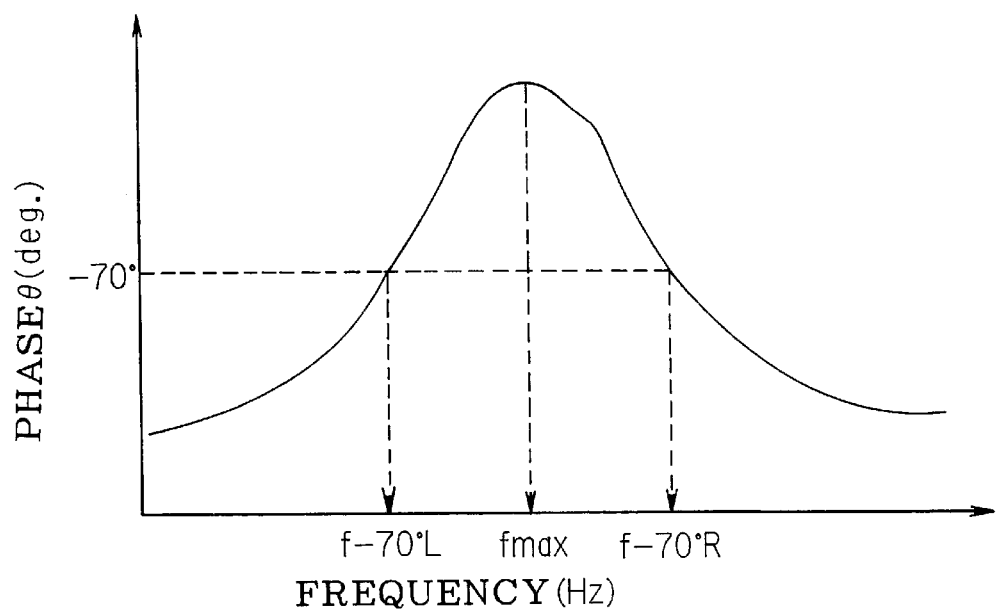
FIG. 5 is an explanatory view explaining the detecting method in the examples based on the graph plotting changes in phases corresponding to frequency.
Figure 6:
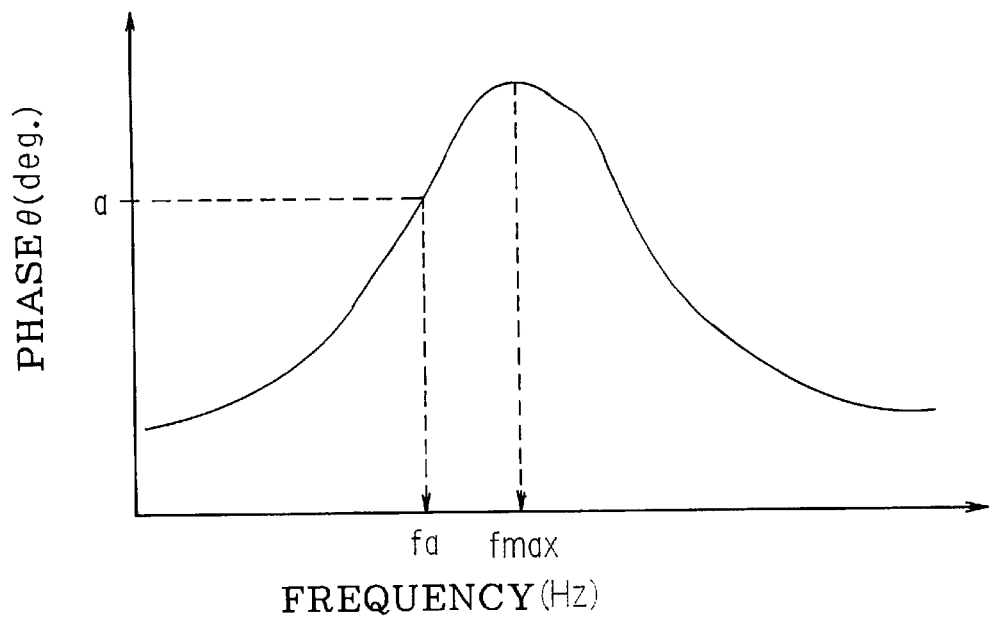
FIG. 6 is an explanatory view explaining the detecting method using the conventional devices based on the graph plotting change in phase corresponding to frequency.
Figure 7:
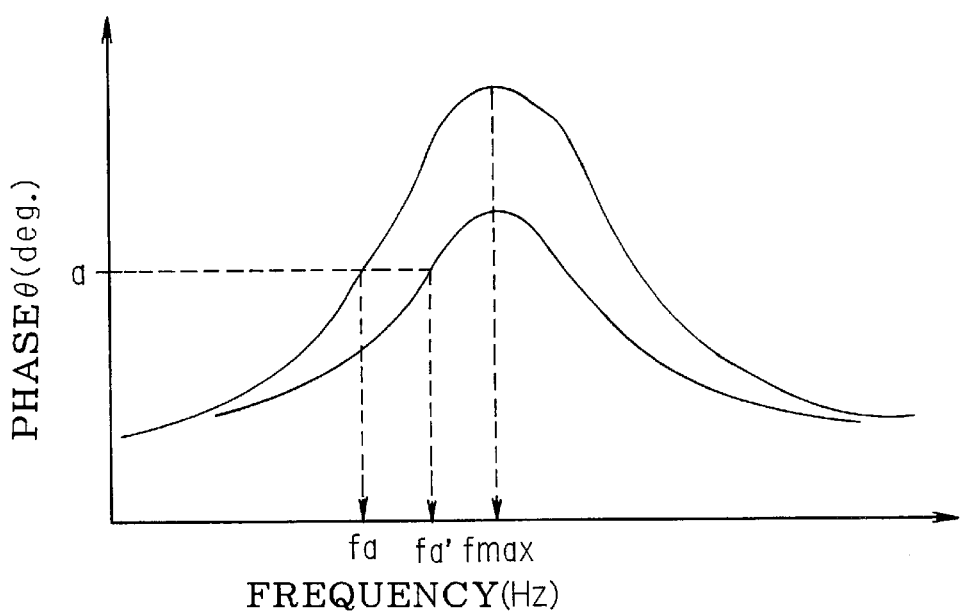
FIG. 7 is a graph plotting change in phase corresponding to frequency showing the state when the vibration characteristics of the vibration system change.

Using a piezoelectric sensor device comprising a sensor element with a structure shown in FIG. 4, and based on the graph (FIG. 5) plotting the change in phase vs. frequency, the following three kinds of detecting methods A through C were conducted for ten measurements each, involving 40%-$H_2SO_4$ as a fluid to be measured, and dispersion (the difference between the largest value and the smallest value) of the measured values) in measured values in each detecting method was examined. The results are shown in Table 1.

Detecting Method A

The frequency $f_{max}$ being the vibration of the piezoelectric body when its phase θ reached maximum was measured.

Detecting Method B

Only $f_{-70° L}$, being the frequency of vibration of the piezoelectric body when its phase θ was −70° and being located left, next to the frequency $f_{max}$ giving a maximum value of θ, was measured.

Detecting Method C $f_{-70° L}$, being the frequency of vibration of the piezoelectric body when its phase θ was −70° and being located left, next to the frequency $f_{max}$ giving a maximum value of θ, as well as $f_{-ξ° R}$, being located right, were measured and the average value of the both $(f_{-ξ° L}+f_{-ξ° R})/2$ was calculated.

TABLE 1

| Detecting method | Frequency (Hz) | Dispersion (Hz) |
|---|---|---|
| A | 150000 | 700 |
| B | 145000 | 450 |
| C | 150000 | 150 |

As shown in Table 1, it is found that dispersion in the detecting method C which can be performed with a device according to the invention gets smaller compared with the detecting method A and the detecting method B which have been conventionally conducted.

Example 2

Using a sensor device with a piezoelectric body vibrator having a polarization state more apt to change than that in piezoelectric sensor device used in the above-described example 1, ten measurements each, involving 40%-$H_2SO_4$ as a fluid to be measured were performed, under a condition where polarization processing was not provided to the piezoelectric body vibrator in the detecting method C in the above-described example 1 as well as under a condition where polarization processing or polarization processing as well as discharging processing were provided in the following four kinds of processing methods A through D, and dispersion (the difference between the largest value and the smallest value of the measured values) in measured values in each processing method was examined. The results are shown in Table 2.

Processing Method A

Measurement was performed with an electric field of 30V being applied to the piezoelectric body.

Processing Method B

Measurement was performed after an electric field of 30V had been applied to the piezoelectric body for one second and thereafter one second had lapsed.

Processing Method C

Measurement was performed after an electric field of 30V had been applied to the piezoelectric body for one second and subsequently both the terminals of the piezoelectric body vibrator had been short circuited for one second and thereafter one second had lapsed.

Processing Method D

Measurement was performed after an electric field of −30V had been applied to the piezoelectric body for one second, and subsequently an electric field of 30V had been applied for one second and further subsequently the both terminals of the piezoelectric body vibrator had been short circuited for one second and thereafter one second had lapsed.

TABLE 2

| Processing Method | Dispersion (Hz) |
|---|---|
| Without Processing | 400 |
| A | 30 |
| B | 50 |
| C | 25 |
| D | 20 |

As shown in Table 2, it is found that dispersion in the measured values gets smaller compared with the case without processing when a condition where polarization processing or polarization processing as well as discharging processing were provided in the above-described processing methods A through D.

As explained above, according to the present invention, vibration characteristics of the vibration system and dispersion in measured values due to change in the polarization state of the piezoelectric body vibrator can be made reduced and thus accuracy in detection can be improved.

What is claimed is:

1. A piezoelectric sensor device comprising:
    a piezoelectric body vibrator including a piezoelectric body sandwiched by a pair of electrodes;
    a power source which applies a voltage to said piezoelectric body vibrator to vibrate said vibrator body;
    means for changing the frequency of vibration of said vibrator between at least two frequency values at which an electric constant of the piezoelectric vibrator body is the same; and
    means for determining the resonance frequency of vibration of said piezoelectric vibrator body by taking an average of said at least two frequency values.

2. The piezoelectric sensor device according to claim 1, wherein the electric constant is one selected from the group consisting of loss factor, phase, resistance, reactance, conductance, susceptance, inductance, and capacitance.

3. The piezoelectric sensor device according to claim 1, further comprising a sensor element comprising the piezoelectric body vibrator and a base body having a thin-plate-shaped vibration section on one surface on which the piezoelectric body vibrator is fixed and a cavity for holding a fluid against the other surface of the vibration section.

4. The piezoelectric sensor device according to claim 1, further comprising means for keeping the polarization state of the piezoelectric body vibrator constant.

5. The piezoelectric sensor device according to claim 4, wherein the means for keeping the polarization state of the piezoelectric body vibrator constant is a power source for polarization processing the piezoelectric body vibrator.

6. The piezoelectric sensor device according to claim 5, further comprising means for discharging electric charge stored in the piezoelectric body after the polarization processing.

7. A method for detecting the resonance frequency of a piezoelectric sensor device, comprising:
    using a piezoelectric sensor device comprising: a piezoelectric body vibrator consisting of a piezoelectric body sandwiched by a pair of electrodes; a power source which applies a voltage to said piezoelectric body vibrator so as to vibrate said vibrator body; means for changing the frequency of vibration of said vibrator between at least two frequency values at which an electric constant of the piezoelectric vibrator body is the same; and means for determining the resonance frequency of vibration of said piezoelectric vibrator body by taking an average of said at least two frequency values, and
    wherein said at least two frequency values are greater than and less than the resonance frequency of vibration of said piezoelectric vibrator body.

8. A method for detecting the resonance frequency of a piezoelectric sensor device, comprising:
    using a piezoelectric sensor device comprising: a piezoelectric body vibrator consisting of a piezoelectric body sandwiched by a pair of electrodes; a power source which applies a voltage to said piezoelectric body vibrator so as to vibrate said vibrator body; means for changing the frequency of vibration of said vibrator between at least two frequency values at which an electric constant of the piezoelectric vibrator body is the same; and means for determining the resonance frequency of vibration of said piezoelectric vibrator body by taking an average of said at least two frequency values, and performing measurement of the frequency values while applying an electric field surpassing the coercive field of the piezoelectric body.

9. A method for detecting the resonance frequency of a piezoelectric sensor device, comprising:

using a piezoelectric sensor device comprising: a piezoelectric body vibrator consisting of a piezoelectric body sandwiched by a pair of electrodes; a power source which applies a voltage to said piezoelectric body vibrator so as to vibrate said vibrator body; means for changing the frequency of vibration of said vibrator between at least two frequency values at which an electric constant of the piezoelectric vibrator body is the same; means for determining the resonance frequency of vibration of said piezoelectric vibrator body by taking an average of said at least two frequency values; means for keeping the polarization state of the piezoelectric body vibrator constant; and a power source making polarization processing take place on the piezoelectric body vibrator, as means for keeping the polarization state of the piezoelectric body vibrator constant, and proceeding with polarization processing with the power source making polarization processing take place on the piezoelectric body vibrator whenever frequency is being measured.

10. The detecting method according to claim 9, wherein the polarization processing is performed by applying an electric field surpassing the coercive field of the piezoelectric body at room temperature for not more than three seconds.

11. The detecting method according to claim 9, wherein the polarization processing is performed by applying an electric field surpassing the coercive field of the piezoelectric body at room temperature for not more than three seconds in one polarity, and thereafter further applying for not more than three seconds in the opposite polarity.

12. The detecting method according to claim 9, wherein measurement of the frequency is conducted after a certain time period has lapsed after the polarization processing has been performed.

13. A method to detect the resonance frequency of a piezoelectric sensor device, comprising:

using a piezoelectric sensor device comprising: a piezoelectric body vibrator consisting of a piezoelectric body sandwiched by a pair of electrodes; a power source which applies a voltage to said piezoelectric body vibrator so as to vibrate said vibrator body; means for changing the frequency of vibration of said vibrator between at least two frequency values at which an electric constant of the piezoelectric vibrator body is the same; means for determining the resonance frequency value of vibration of said piezoelectric vibrator body by taking an average of said at least two frequency values; means for keeping the polarization state of the piezoelectric body vibrator constant; a power source making polarization processing take place on the piezoelectric body vibrator, as means for keeping the polarization state of the piezoelectric body vibrator constant; and means for discharging the electric charge stored in the piezoelectric body after the polarization processing, and discharging the electric charge stored in the piezoelectric body after the polarization processing is performed by means for discharging the electric charge stored in the piezoelectric body after the polarization processing.

14. The detecting method according to claim 13, wherein measurement of the frequency is conducted after a certain time period has lapsed after the discharging processing has been performed.

* * * * *